(12) United States Patent
Trieu

(10) Patent No.: US 7,682,376 B2
(45) Date of Patent: Mar. 23, 2010

(54) INTERSPINOUS DEVICES AND METHODS OF USE

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 96 days.

(21) Appl. No.: 11/341,200

(22) Filed: Jan. 27, 2006

(65) Prior Publication Data

US 2007/0191837 A1    Aug. 16, 2007

(51) Int. Cl.
*A61B 17/70*    (2006.01)
(52) U.S. Cl. .................. 606/248; 623/17.13; 623/17.15
(58) Field of Classification Search .................. 606/61, 606/246, 248, 249; 623/17.11–17.16; 482/11, 482/44, 49
See application file for complete search history.

(56) References Cited

U.S. PATENT DOCUMENTS

| | | | |
|---|---|---|---|
| 2,677,369 A | 5/1954 | Knowles | |
| 2,837,334 A * | 6/1958 | Long ........................ | 482/49 |
| 3,648,691 A | 3/1972 | Lumb et al. | |
| 4,011,602 A | 3/1977 | Rybicki et al. | |
| 4,257,409 A | 3/1981 | Bacal et al. | |
| 4,554,914 A | 11/1985 | Kapp et al. | |
| 4,573,454 A | 3/1986 | Hoffman | |
| 4,604,995 A | 8/1986 | Stephens et al. | |
| 4,657,550 A | 4/1987 | Daher | |
| 4,686,970 A | 8/1987 | Dove et al. | |
| 4,743,260 A | 5/1988 | Burton | |
| 4,827,918 A | 5/1989 | Olerud | |
| 4,863,476 A | 9/1989 | Shepperd | |
| 4,931,055 A | 6/1990 | Bumpus et al. | |
| 5,011,484 A | 4/1991 | Breard | |
| 5,047,055 A | 9/1991 | Bao et al. | |
| 5,059,193 A | 10/1991 | Kuslich | |
| 5,092,866 A | 3/1992 | Breard et al. | |
| 5,098,433 A | 3/1992 | Freedland | |
| 5,171,278 A | 12/1992 | Pisharodi | |

(Continued)

FOREIGN PATENT DOCUMENTS

DE    2821678 A1    11/1979

(Continued)

OTHER PUBLICATIONS

Trieu, Hai H., "Intervertebral Implants and Methods of Use." Filed on Jan. 27, 2006, 29 pages, U.S. Appl. No. 11/340,972.

(Continued)

*Primary Examiner*—Thomas C Barrett
*Assistant Examiner*—Andrew Yang
(74) *Attorney, Agent, or Firm*—Coats and Bennett, P.L.L.C.

(57) ABSTRACT

Devices and methods for spacing the spinous processes of adjacent vertebral members. In one embodiment, the device includes first and second sections and an intermediate section that together form an interior section. An elastic member may be positioned within the interior section. The elastic member may have a variety of orientations, sizes, shapes, densities, modulus of elasticity, and other material properties depending upon the desired displacement between the first and second sections. The intermediate section in combination with the elastic member may be deformed during this movement and thereby exert a force to stabilize the vertebral members.

2 Claims, 9 Drawing Sheets

U.S. PATENT DOCUMENTS

| | | | |
|---|---|---|---|
| 5,180,393 A | 1/1993 | Commarmond | |
| 5,201,734 A | 4/1993 | Cozad et al. | |
| 5,282,863 A | 2/1994 | Burton | |
| 5,306,275 A | 4/1994 | Bryan | |
| 5,360,430 A | 11/1994 | Lin | |
| 5,366,455 A | 11/1994 | Dove | |
| 5,375,823 A | 12/1994 | Navas | |
| 5,390,683 A | 2/1995 | Pisharodi | |
| 5,395,370 A | 3/1995 | Muller et al. | |
| 5,415,661 A | 5/1995 | Holmes | |
| 5,423,816 A | 6/1995 | Lin | |
| 5,437,672 A | 8/1995 | Alleyne | |
| 5,454,812 A | 10/1995 | Lin | |
| 5,458,642 A | 10/1995 | Beer et al. | |
| 5,480,401 A | 1/1996 | Navas | |
| 5,496,318 A | 3/1996 | Howland et al. | |
| 5,518,498 A | 5/1996 | Lindenberg et al. | |
| 5,540,688 A | 7/1996 | Navas | |
| 5,554,191 A | 9/1996 | Lahille et al. | |
| 5,562,737 A | 10/1996 | Graf | |
| 5,584,834 A | 12/1996 | Errico et al. | |
| 5,609,634 A | 3/1997 | Voydeville | |
| 5,609,635 A | 3/1997 | Michelson | |
| 5,628,756 A | 5/1997 | Barker, Jr. et al. | |
| 5,645,599 A * | 7/1997 | Samani | 623/17.16 |
| 5,665,122 A | 9/1997 | Kambin | |
| 5,672,175 A | 9/1997 | Martin | |
| 5,674,295 A | 10/1997 | Ray et al. | |
| 5,676,702 A * | 10/1997 | Ratron | 623/17.16 |
| 5,690,649 A | 11/1997 | Li | |
| 5,702,450 A | 12/1997 | Bisserie | |
| 5,702,455 A | 12/1997 | Saggar | |
| 5,704,936 A | 1/1998 | Mazel | |
| 5,707,390 A | 1/1998 | Bonutti | |
| 5,713,899 A | 2/1998 | Marnay et al. | |
| 5,716,416 A | 2/1998 | Lin | |
| 5,733,284 A | 3/1998 | Martin | |
| 5,749,916 A | 5/1998 | Richelsoph | |
| 5,810,815 A | 9/1998 | Morales | |
| 5,836,948 A | 11/1998 | Zucherman et al. | |
| 5,860,977 A | 1/1999 | Zucherman et al. | |
| 5,928,284 A | 7/1999 | Mehdizadeh | |
| 5,961,516 A | 10/1999 | Graf | |
| 5,976,186 A | 11/1999 | Bao et al. | |
| 5,993,448 A | 11/1999 | Remmler | |
| 6,022,376 A | 2/2000 | Assell et al. | |
| 6,048,342 A | 4/2000 | Zucherman et al. | |
| 6,068,630 A | 5/2000 | Zucherman et al. | |
| 6,126,689 A | 10/2000 | Brett | |
| 6,127,597 A | 10/2000 | Beyar et al. | |
| 6,132,464 A | 10/2000 | Martin | |
| 6,190,414 B1 | 2/2001 | Young | |
| 6,214,050 B1 | 4/2001 | Huene | |
| 6,231,609 B1 * | 5/2001 | Mehdizadeh | 623/17.13 |
| 6,241,730 B1 | 6/2001 | Alby | |
| 6,248,106 B1 | 6/2001 | Ferree | |
| 6,267,764 B1 | 7/2001 | Elberg | |
| 6,293,949 B1 | 9/2001 | Justis et al. | |
| 6,296,643 B1 | 10/2001 | Hopf et al. | |
| 6,352,537 B1 | 3/2002 | Strnad | |
| 6,364,883 B1 | 4/2002 | Santilli | |
| 6,375,682 B1 | 4/2002 | Fleischmann et al. | |
| 6,387,134 B1 * | 5/2002 | Parker et al. | 623/55 |
| 6,402,750 B1 | 6/2002 | Atkinson et al. | |
| 6,419,704 B1 | 7/2002 | Ferree | |
| 6,419,706 B1 * | 7/2002 | Graf | 623/17.16 |
| 6,440,169 B1 | 8/2002 | Elberg et al. | |
| 6,451,019 B1 | 9/2002 | Zucherman et al. | |
| 6,478,796 B2 | 11/2002 | Zucherman et al. | |
| 6,488,710 B2 * | 12/2002 | Besselink | 623/17.15 |
| 6,514,256 B2 | 2/2003 | Zucherman | |
| 6,520,991 B2 | 2/2003 | Huene | |
| 6,527,804 B1 * | 3/2003 | Gauchet et al. | 623/17.12 |
| 6,527,806 B2 | 3/2003 | Ralph et al. | |
| 6,540,785 B1 | 4/2003 | Gill et al. | |
| 6,554,833 B2 | 4/2003 | Levy | |
| 6,582,433 B2 | 6/2003 | Yun | |
| 6,582,466 B1 * | 6/2003 | Gauchet | 623/17.11 |
| 6,582,467 B1 | 6/2003 | Teitelbaum et al. | |
| 6,616,669 B2 | 9/2003 | Ogilvie et al. | |
| 6,626,904 B1 | 9/2003 | Jamm et al. | |
| 6,626,944 B1 | 9/2003 | Taylor | |
| 6,645,207 B2 | 11/2003 | Dixon et al. | |
| 6,685,742 B1 | 2/2004 | Jackson | |
| 6,695,842 B2 | 2/2004 | Zucherman et al. | |
| 6,706,044 B2 | 3/2004 | Kuslich et al. | |
| 6,709,435 B2 | 3/2004 | Lin | |
| 6,723,126 B1 | 4/2004 | Berry | |
| 6,730,126 B2 | 5/2004 | Boehm, Jr. et al. | |
| 6,733,534 B2 | 5/2004 | Sherman | |
| 6,736,818 B2 | 5/2004 | Perren et al. | |
| 6,743,257 B2 | 6/2004 | Castro | |
| 6,758,863 B2 | 7/2004 | Estes et al. | |
| 6,761,720 B1 | 7/2004 | Senegas | |
| 6,783,527 B2 | 8/2004 | Drewry et al. | |
| 6,793,679 B2 | 9/2004 | Michelson | |
| 6,796,983 B1 | 9/2004 | Zucherman et al. | |
| 6,835,205 B2 | 12/2004 | Atkinson et al. | |
| 6,893,466 B2 | 5/2005 | Trieu | |
| 6,905,512 B2 | 6/2005 | Paes et al. | |
| 6,946,000 B2 | 9/2005 | Senegas et al. | |
| 6,766,910 B1 | 11/2005 | Ritland | |
| 6,966,910 B2 | 11/2005 | Ritland | |
| 6,981,975 B2 | 1/2006 | Michelson | |
| 6,986,771 B2 | 1/2006 | Paul et al. | |
| 6,989,011 B2 | 1/2006 | Paul et al. | |
| 6,991,632 B2 | 1/2006 | Ritland | |
| 7,011,685 B2 | 3/2006 | Arnin et al. | |
| 7,018,379 B2 | 3/2006 | Drewry et al. | |
| 7,029,475 B2 | 4/2006 | Panjabi | |
| 7,041,136 B2 | 5/2006 | Goble et al. | |
| 7,048,736 B2 | 5/2006 | Robinson et al. | |
| 7,052,515 B2 * | 5/2006 | Simonson | 623/17.13 |
| 7,066,957 B2 | 6/2006 | Graf | |
| 7,081,120 B2 | 7/2006 | Li et al. | |
| 7,083,621 B2 | 8/2006 | Shaolian et al. | |
| 7,083,622 B2 | 8/2006 | Simonson | |
| 7,087,083 B2 | 8/2006 | Pasquet et al. | |
| 7,097,648 B1 | 8/2006 | Globerman et al. | |
| 7,125,410 B2 | 10/2006 | Freudiger | |
| 7,137,985 B2 | 11/2006 | Jahng | |
| 7,156,848 B2 * | 1/2007 | Ferree | 606/61 |
| 7,163,558 B2 | 1/2007 | Senegas et al. | |
| 7,201,751 B2 | 4/2007 | Zucherman et al. | |
| 7,217,293 B2 | 5/2007 | Branch, Jr. | |
| 7,238,204 B2 | 7/2007 | Le Couedic et al. | |
| 7,291,150 B2 | 11/2007 | Graf | |
| 7,306,628 B2 | 12/2007 | Zucherman et al. | |
| 7,326,210 B2 | 2/2008 | Jahng et al. | |
| 7,329,258 B2 | 2/2008 | Studer | |
| 7,338,525 B2 | 3/2008 | Ferree | |
| 7,361,196 B2 | 4/2008 | Fallin et al. | |
| 7,377,921 B2 | 5/2008 | Studer et al. | |
| 7,442,208 B2 | 10/2008 | Mathieu et al. | |
| 7,445,637 B2 | 11/2008 | Taylor | |
| 2001/0007073 A1 | 7/2001 | Zucherman et al. | |
| 2002/0133155 A1 | 9/2002 | Ferree | |
| 2002/0143331 A1 | 10/2002 | Zucherman et al. | |
| 2003/0109880 A1 | 6/2003 | Shirado et al. | |
| 2003/0114853 A1 | 6/2003 | Burgess et al. | |
| 2003/0153915 A1 | 8/2003 | Nekozuka et al. | |
| 2003/0171749 A1 | 9/2003 | Le Couedic et al. | |
| 2003/0191470 A1 * | 10/2003 | Ritland | 606/61 |
| 2003/0220643 A1 | 11/2003 | Ferree | |

| | | | | | | |
|---|---|---|---|---|---|---|
| 2004/0002708 A1 | 1/2004 | Ritland | | 2006/0089654 A1 | 4/2006 | Lins et al. |
| 2004/0006343 A1 | 1/2004 | Sevrain | | 2006/0089719 A1 | 4/2006 | Trieu |
| 2004/0049189 A1 | 3/2004 | Le Couedic et al. | | 2006/0106381 A1 | 5/2006 | Ferree et al. |
| 2004/0049190 A1 | 3/2004 | Biedermann et al. | | 2006/0106397 A1 | 5/2006 | Lins |
| 2004/0073215 A1* | 4/2004 | Carli .................... 606/61 | | 2006/0111728 A1 | 5/2006 | Abdou |
| 2004/0097931 A1 | 5/2004 | Mitchell | | 2006/0116690 A1 | 6/2006 | Pagano |
| 2004/0106995 A1 | 6/2004 | Le Couedic et al. | | 2006/0122620 A1 | 6/2006 | Kim |
| 2004/0133204 A1 | 7/2004 | Davies | | 2006/0136060 A1 | 6/2006 | Taylor |
| 2004/0143264 A1 | 7/2004 | McAfee | | 2006/0142758 A1 | 6/2006 | Petit |
| 2004/0147928 A1 | 7/2004 | Landry et al. | | 2006/0142760 A1 | 6/2006 | McDonnell |
| 2004/0167625 A1 | 8/2004 | Beyar et al. | | 2006/0184171 A1 | 8/2006 | Biedermann et al. |
| 2004/0215191 A1 | 10/2004 | Kitchen | | 2006/0184247 A1 | 8/2006 | Edidin et al. |
| 2004/0236329 A1 | 11/2004 | Panjabi | | 2006/0184248 A1 | 8/2006 | Edidin et al. |
| 2004/0243239 A1 | 12/2004 | Taylor | | 2006/0189985 A1 | 8/2006 | Lewis |
| 2004/0260397 A1 | 12/2004 | Lambrecht et al. | | 2006/0195093 A1 | 8/2006 | Jahng |
| 2004/0267260 A1 | 12/2004 | Mack et al. | | 2006/0195102 A1 | 8/2006 | Malandain |
| 2005/0010293 A1 | 1/2005 | Zucherman et al. | | 2006/0212033 A1 | 9/2006 | Rothman et al. |
| 2005/0043796 A1 | 2/2005 | Grant et al. | | 2006/0217726 A1 | 9/2006 | Maxy et al. |
| 2005/0049708 A1 | 3/2005 | Atkinson | | 2006/0022968 A1 | 10/2006 | Foster et al. |
| 2005/0065516 A1 | 3/2005 | Jahng | | 2006/0229612 A1 | 10/2006 | Rothman et al. |
| 2005/0085815 A1 | 4/2005 | Harms | | 2006/0241765 A1* | 10/2006 | Burn et al. ............. 623/17.12 |
| 2005/0113927 A1 | 5/2005 | Malek | | 2006/0247632 A1 | 11/2006 | Winslow et al. |
| 2005/0124991 A1 | 6/2005 | Jahng | | 2006/0247637 A1 | 11/2006 | Colleran et al. |
| 2005/0125063 A1 | 6/2005 | Matge et al. | | 2006/0264935 A1 | 11/2006 | White |
| 2005/0131407 A1 | 6/2005 | Sicvol et al. | | 2006/0264937 A1 | 11/2006 | White |
| 2005/0143737 A1 | 6/2005 | Pafford et al. | | 2006/0264938 A1 | 11/2006 | Zucherman et al. |
| 2005/0143823 A1 | 6/2005 | Boyd et al. | | 2006/0271044 A1 | 11/2006 | Petrini et al. |
| 2005/0143827 A1 | 6/2005 | Globerman et al. | | 2006/0276790 A1 | 12/2006 | Dawson et al. |
| 2005/0149020 A1 | 7/2005 | Jahng | | 2006/0282080 A1 | 12/2006 | Albert et al. |
| 2005/0149023 A1 | 7/2005 | Ritland | | 2006/0293657 A1 | 12/2006 | Hartmann |
| 2005/0154390 A1 | 7/2005 | Biedermann et al. | | 2006/0293662 A1 | 12/2006 | Boyer, II et al. |
| 2005/0165396 A1 | 7/2005 | Fortin et al. | | 2007/0016190 A1 | 1/2007 | Martinez et al. |
| 2005/0165398 A1 | 7/2005 | Reiley | | 2007/0016193 A1 | 1/2007 | Ritland |
| 2005/0171540 A1 | 8/2005 | Lim | | 2007/0016200 A1 | 1/2007 | Jackson |
| 2005/0171543 A1 | 8/2005 | Timm et al. | | 2007/0016201 A1 | 1/2007 | Freudiger |
| 2005/0177156 A1 | 8/2005 | Timm et al. | | 2007/0043356 A1 | 2/2007 | Timm et al. |
| 2005/0177157 A1 | 8/2005 | Jahng | | 2007/0049936 A1 | 3/2007 | Colleran et al. |
| 2005/0177164 A1 | 8/2005 | Walters et al. | | 2007/0049937 A1 | 3/2007 | Matthis et al. |
| 2005/0182400 A1 | 8/2005 | White | | 2007/0055247 A1 | 3/2007 | Jahng |
| 2005/0182401 A1 | 8/2005 | Timm et al. | | 2007/0073289 A1 | 3/2007 | Kwak et al. |
| 2005/0182409 A1 | 8/2005 | Callahan et al. | | 2007/0088359 A1 | 4/2007 | Woods et al. |
| 2005/0203512 A1 | 9/2005 | Hawkins et al. | | 2007/0100341 A1 | 5/2007 | Reglos et al. |
| 2005/0203513 A1 | 9/2005 | Jahng et al. | | 2007/0123871 A1 | 5/2007 | Jahng |
| 2005/0203514 A1 | 9/2005 | Jahng et al. | | 2007/0129729 A1 | 6/2007 | Petit et al. |
| 2005/0203518 A1 | 9/2005 | Biedermann et al. | | 2007/0151116 A1 | 7/2007 | Malandain |
| 2005/0203519 A1 | 9/2005 | Harms et al. | | 2007/0167945 A1* | 7/2007 | Lange et al. ............. 606/61 |
| 2005/0203624 A1* | 9/2005 | Serhan et al. ........ 623/17.11 | | 2007/0198088 A1 | 8/2007 | Biedermann et al. |
| 2005/0209694 A1 | 9/2005 | Loeb | | 2007/0213719 A1 | 9/2007 | Hudgins et al. |
| 2005/0222569 A1 | 10/2005 | Panjabi | | 2007/0225710 A1 | 9/2007 | Jahng et al. |
| 2005/0228391 A1 | 10/2005 | Levy et al. | | 2007/0233064 A1 | 10/2007 | Holt |
| 2005/0261685 A1 | 11/2005 | Fortin et al. | | 2007/0270860 A1 | 11/2007 | Jackson |
| 2005/0261686 A1 | 11/2005 | Paul | | 2007/0276380 A1 | 11/2007 | Jahng et al. |
| 2005/0261768 A1 | 11/2005 | Trieu | | 2007/0282443 A1 | 12/2007 | Globerman et al. |
| 2005/0277922 A1 | 12/2005 | Trieu | | 2007/0288008 A1 | 12/2007 | Park |
| 2005/0277934 A1 | 12/2005 | Vardiman | | 2007/0288093 A1 | 12/2007 | Le Couedic et al. |
| 2005/0288670 A1 | 12/2005 | Panjabi et al. | | 2007/0293862 A1 | 12/2007 | Jackson |
| 2005/0288672 A1 | 12/2005 | Ferree | | 2008/0021459 A1 | 1/2008 | Lim |
| 2006/0004447 A1 | 1/2006 | Mastrorio et al. | | 2008/0033435 A1 | 2/2008 | Studer et al. |
| 2006/0004455 A1 | 1/2006 | Leonard et al. | | 2008/0039943 A1 | 2/2008 | Le Couedic |
| 2006/0009768 A1 | 1/2006 | Ritland | | 2008/0045951 A1 | 2/2008 | Fanger et al. |
| 2006/0015181 A1 | 1/2006 | Elberg | | 2008/0097431 A1 | 4/2008 | Vessa |
| 2006/0036240 A1 | 2/2006 | Colleran et al. | | 2008/0097434 A1 | 4/2008 | Moumene et al. |
| 2006/0041259 A1 | 2/2006 | Paul et al. | | 2008/0140076 A1 | 6/2008 | Jackson |
| 2006/0064090 A1 | 3/2006 | Park | | 2008/0147122 A1 | 6/2008 | Jackson |
| 2006/0064165 A1 | 3/2006 | Zucherman et al. | | 2008/0154307 A1 | 6/2008 | Colleran et al. |
| 2006/0084982 A1 | 4/2006 | Kim | | | | |
| 2006/0084983 A1 | 4/2006 | Kim | | | | |
| 2006/0084984 A1 | 4/2006 | Kim | | | | |

FOREIGN PATENT DOCUMENTS

| | | |
|---|---|---|
| 2006/0084985 A1 | 4/2006 Kim | |
| 2006/0084987 A1 | 4/2006 Kim | |
| 2006/0084988 A1 | 4/2006 Kim | |
| 2006/0084991 A1 | 4/2006 Borgstrom et al. | |
| 2006/0085069 A1 | 4/2006 Kim | |

| | | | |
|---|---|---|---|
| DE | 3922044 | A1 | 2/1991 |
| DE | 4012622 | C1 | 7/1991 |
| DE | 43 15 757 | C1 | 11/1994 |
| EP | 0322334 | B1 | 2/1992 |
| EP | 0 642 775 | | 3/1995 |

| | | | |
|---|---|---|---|
| EP | 0767636 B1 | 1/1999 | |
| EP | 1004276 A1 | 5/2000 | |
| EP | 1138268 A1 | 10/2001 | |
| EP | 1 287 794 | 3/2003 | |
| FR | 2623085 A1 | 5/1989 | |
| FR | 2625097 A1 | 6/1989 | |
| FR | 2681525 A1 | 3/1993 | |
| FR | 2700941 A1 | 8/1994 | |
| FR | 2703239 A1 | 10/1994 | |
| FR | 2707864 A1 | 1/1995 | |
| FR | 2717675 A1 | 9/1995 | |
| FR | 2722087 A1 | 1/1996 | |
| FR | 2722088 A1 | 1/1996 | |
| FR | 2 722 980 | 2/1996 | |
| FR | 2724554 A1 | 3/1996 | |
| FR | 2725892 A1 | 4/1996 | |
| FR | 2730156 A1 | 8/1996 | |
| FR | 2731643 A1 | 9/1996 | |
| FR | 2 774 581 | 8/1999 | |
| FR | 2775183 A1 | 8/1999 | |
| FR | 2816197 A1 | 5/2002 | |
| FR | 2 844 180 A1 | 12/2004 | |
| FR | 2 860 428 | 4/2005 | |
| JP | 02-224660 | 9/1990 | |
| JP | 09-075381 | 3/1997 | |
| SU | 988281 | 1/1983 | |
| WO | WO 94/26192 | 11/1994 | |
| WO | WO 94/26195 | 11/1994 | |
| WO | WO 98/20939 | 5/1998 | |
| WO | WO 99/26562 | 6/1999 | |
| WO | WO 00/44319 | 8/2000 | |
| WO | WO 01/54598 A1 | 8/2001 | |
| WO | WO 01/62190 A1 | 8/2001 | |
| WO | WO 02/102259 A2 | 12/2002 | |
| WO | WO 03/057055 A1 | 7/2003 | |
| WO | WO 2004/047689 A1 | 6/2004 | |
| WO | WO 2004/047691 A1 | 6/2004 | |
| WO | 2004/089244 | 10/2004 | |
| WO | 2004/105577 | 12/2004 | |
| WO | 2005-011522 | 2/2005 | |
| WO | WO 2005/009300 A1 | 2/2005 | |
| WO | WO 2005/011507 A1 | 2/2005 | |
| WO | WO 2005/044118 A1 | 5/2005 | |
| WO | WO 2005/048856 A1 | 5/2005 | |
| WO | WO 2005/110258 A1 | 11/2005 | |
| WO | 2006/106246 | 10/2006 | |
| WO | WO 2007/034516 A1 | 3/2007 | |

OTHER PUBLICATIONS

Trieu, Hai H., "Vertebral Rods and Methods of Use." Filed on Jan. 27, 2006, 32 pages, U.S. Appl. No. 11/340,973.
"Dispositivo Intervertebrale Ammortizzante DIAM," date unknown, p. 1.
"Tecnica Operatoria Per II Posizionamento Della Protesi DIAM," date unknown, pp. 1-3.
"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.
Benzel et al., "Posterior Cervical Interspinous Compression Wiring and Fusion for Mid to Low Cervical Spinal Injuries," J. Neurosurg., Jun. 1989, pp. 893-899, vol. 70.
Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.
Christie et al., "Dynamic Interspinous Process Technology," SPINE, 2005, pp. S73-S78, vol. 30, No. 16S.
Cousin Biotech, "Analysis of Clinical Experience with a Posterior Shock-Absorbing Implant," date unknown, pp. 2-9.
Cousin Biotech, Dispositif Intervertébral Amortissant, Jun. 1998, pp. 1-4.
Cousin Biotech, Technique Operatoire de la Prothese DIAM, date unknown, Annexe 1, pp. 1-8.
Dickman et al., "The Interspinous Method of Posterior Atlantoaxial Arthrodesis," J. Neurosurg., Feb. 1991, pp. 190-198, vol. 74.
Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.
Ebara et al., "Inoperative Measurement of Lumbar Spinal Instability," SPINE, 1992, pp. S44-S50, vol. 17, No. 3S.
Fassio et al., "Treatment of Degenerative Lumbar Spinal Instability L4-L5 by Interspinous Ligamentoplasty," Rachis, Dec. 1991, pp. 465-474, vol. 3, No. 6.
Fassio, "Mise au Point Sur la Ligamentoplastie Inter-Epineuse Lombaire Dans les Instabilites," Maôitrise Orthopédique, Jul. 1993, pp. 18, No. 25.
Garner et al., "Development and Preclinical Testing of a New Tension-Band Device for the Spine: the Loop System," Eur. Spine J., Aug. 7, 2002, pp. S186-S191, vol. 11, Suppl. 2.
Guang et al., "Interspinous Process Segmental Instrumentation with Bone-Button-Wire for Correction of Scoliosis," Chinese Medical J., 1990, pp. 721-725, vol. 103.
Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.
Hambly et al., "Tension Band Wiring-Bone Grafting for Spondylolysis and Spondylolisthesis," SPINE, 1989, pp. 455-460, vol. 14, No. 4.
Kiwerski, "Rehabilitation of Patients with Thoracic Spine Injury Treated by Spring Alloplasty," Int. J. Rehab. Research, 1983, pp. 469-474, vol. 6, No. 4.
Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.
Mah et al., "Threaded K-Wire Spinous Process Fixation of the Axis for Modified Gallie Fusion in Children and Adolescents," J. Pediatric Othopaedics, 1989, pp. 675-679, vol. 9.
Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.
McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.
Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.
Müller, "Restauration Dynamique de la Stabilité Rachidienne," Tiré de la Sulzer Technical Review, Jan. 1999, Sulzer Management Ltd, Winterthur, Switzerland.
Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.
Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.
Petrini et al., "Stabilizzazione Elastica," Patologia Degenerativa del Rachide Lombare, Oct. 5-6, 2001, Rimini.
Porter, "Spinal Stenosis and Neurogenic Claudication," SPINE, Sep. 1, 1996, pp. 2046-2052, vol. 21, No. 17.
Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.
Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

* cited by examiner

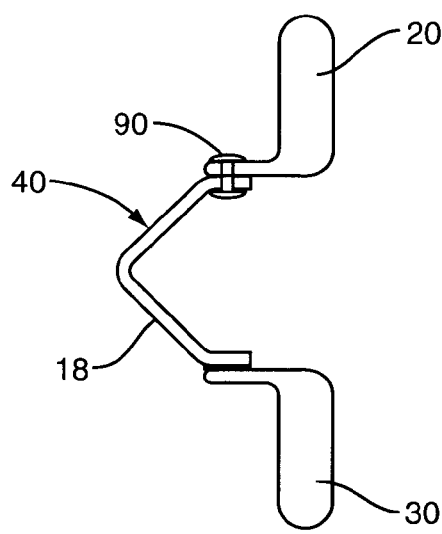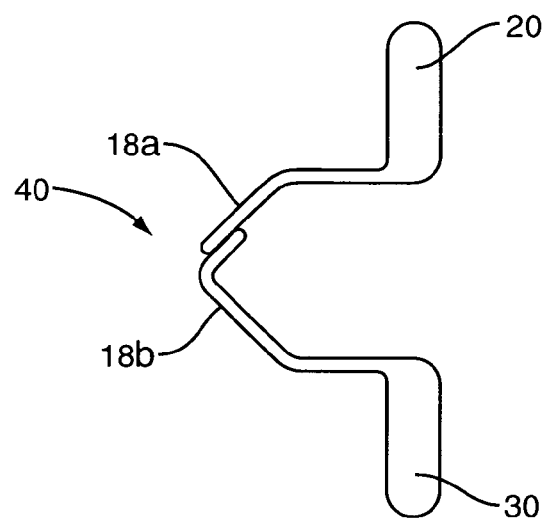
*FIG. 2*  *FIG. 3*
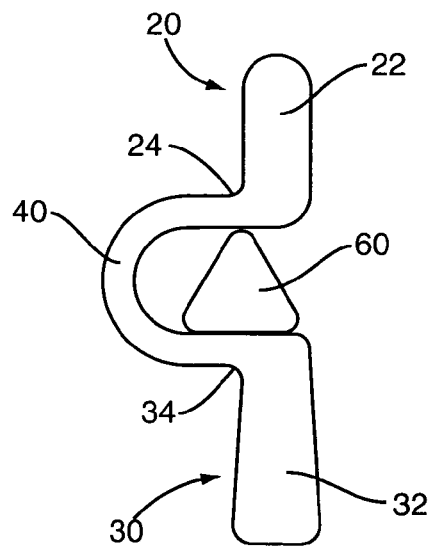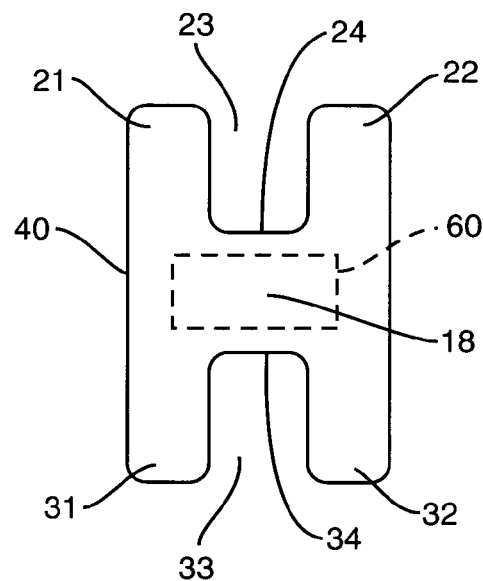
*FIG. 4*  *FIG. 5*

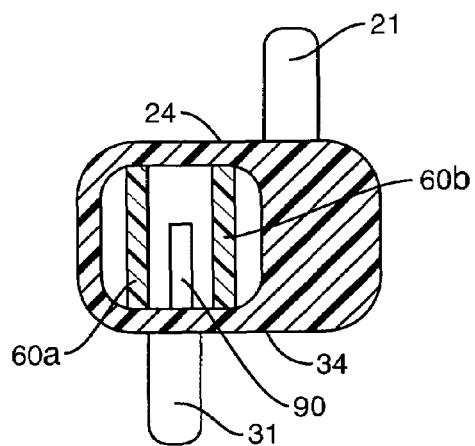
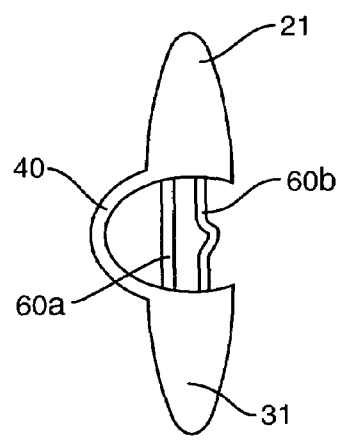
*FIG. 20*  *FIG. 22A*
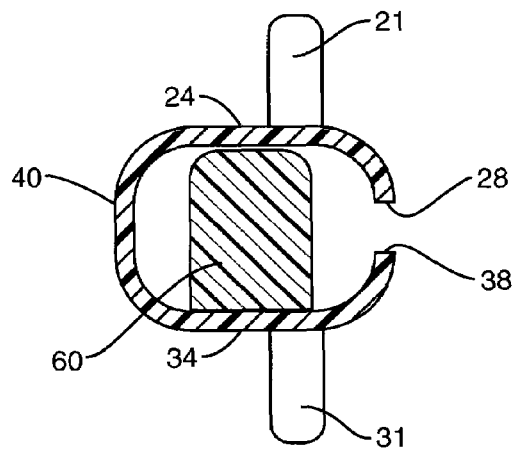
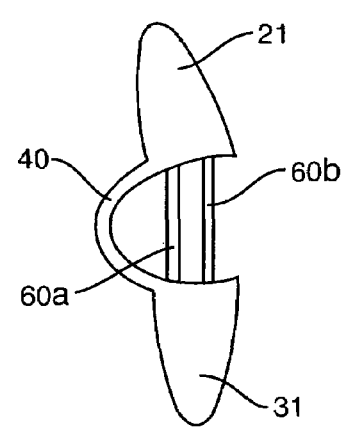
*FIG. 21A*  *FIG. 22B*
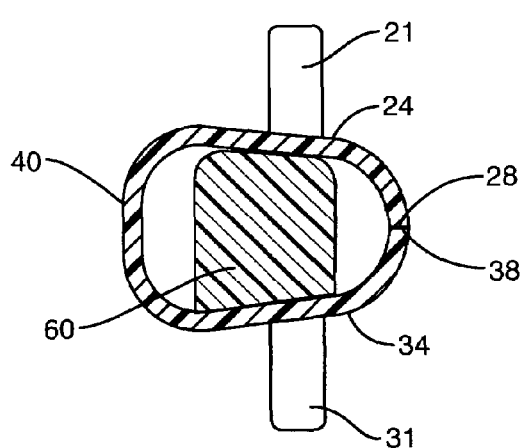
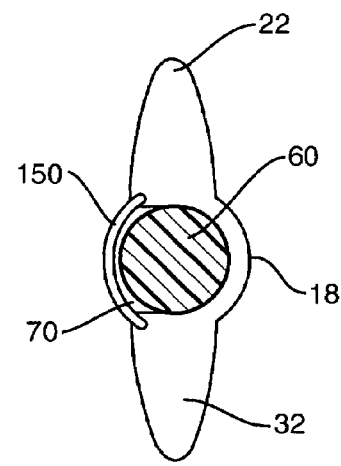
*FIG. 21B*  *FIG. 23*

INTERSPINOUS DEVICES AND METHODS OF USE

BACKGROUND

The present application is directed to devices and methods for stabilizing vertebral members, and more particularly, to interspinous devices positioned between the spinous processes of vertebral members.

Vertebral members comprise a body, pedicles, laminae, and processes. The body has an hourglass shape with a thinner middle section and wider ends, and include sections on the inferior and superior ends. Intervertebral discs are positioned between the bodies of adjacent vertebral members to permit flexion, extension, lateral bending, and rotation. The pedicles are two short rounded members that extend posteriorly from the body, and the laminae are two flattened members that extend medially from the pedicles. The processes are projections that serve as insertion points for the ligaments and tendons. The processes include the articular processes, transverse processes, and the spinous process. The spinous process is a single member that extends posteriorly from the junction of the two lamina. The spinous process acts as a lever to effect motion of the vertebral member.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

One method of correcting the damage is insertion of a device between the spinous processes of adjacent vertebral members. The device may reduce or eliminate the pain and neurological deficit, and increase the range of motion.

SUMMARY

The present application is directed to devices and methods for spacing the spinous processes of adjacent vertebral members. In one embodiment, the device includes first and second sections and an intermediate section that together form an interior section. An elastic member may be positioned within the interior section. The elastic member may have a variety of orientations, sizes, shapes, densities, modulus of elasticity, and other material properties depending upon the desired displacement between the first and second sections.

In use according to one embodiment, the device may assume a first shape when the vertebral members are aligned, such as when the patient is standing erect or in a prone position. This first shape may include the first and second sections spaced a first distance apart. During movement of the vertebral members, the device may be placed in compression or tension. The intermediate section in combination with the elastic member may be deformed during this movement and thereby exert a force to stabilize the vertebral members.

BRIEF DESCRIPTION OF THE DRAWINGS

FIG. 2 is a side schematic view of a body according to one embodiment.

FIG. 3 is a side schematic view of a body according to one embodiment.

FIG. 4 is a side schematic view of a device according to one embodiment.

FIG. 5 is a rear view of a device according to one embodiment.

FIG. 20 is a schematic cross section view of a device according to one embodiment.

FIG. 21A-21B are schematic cross section views of a device according to one embodiment.

FIG. 22A is a side schematic view of a device in a neutral configuration according to one embodiment.

FIG. 22B is a side schematic view of a device with the bases moved outward according to one embodiment.

FIG. 23 is a side schematic view of a device with a tether according to one embodiment.

DETAILED DESCRIPTION

The present application is directed to devices and methods for spacing apart spinous processes of adjacent vertebral members. The device may include a body sized to fit between the adjacent spinous processes. The body may include upper and lower sections and an intermediate section that together form an interior section. An elastic member is positioned within the interior section. The elastic member may have a variety of orientations, sizes, shapes, densities, modulus of elasticity, and other material properties depending upon the desired displacement between the first and second sections. The elastic member and/or the intermediate section may be elastically flexible to exert a stabilizing force during movement of the vertebral members.

Figure 1:
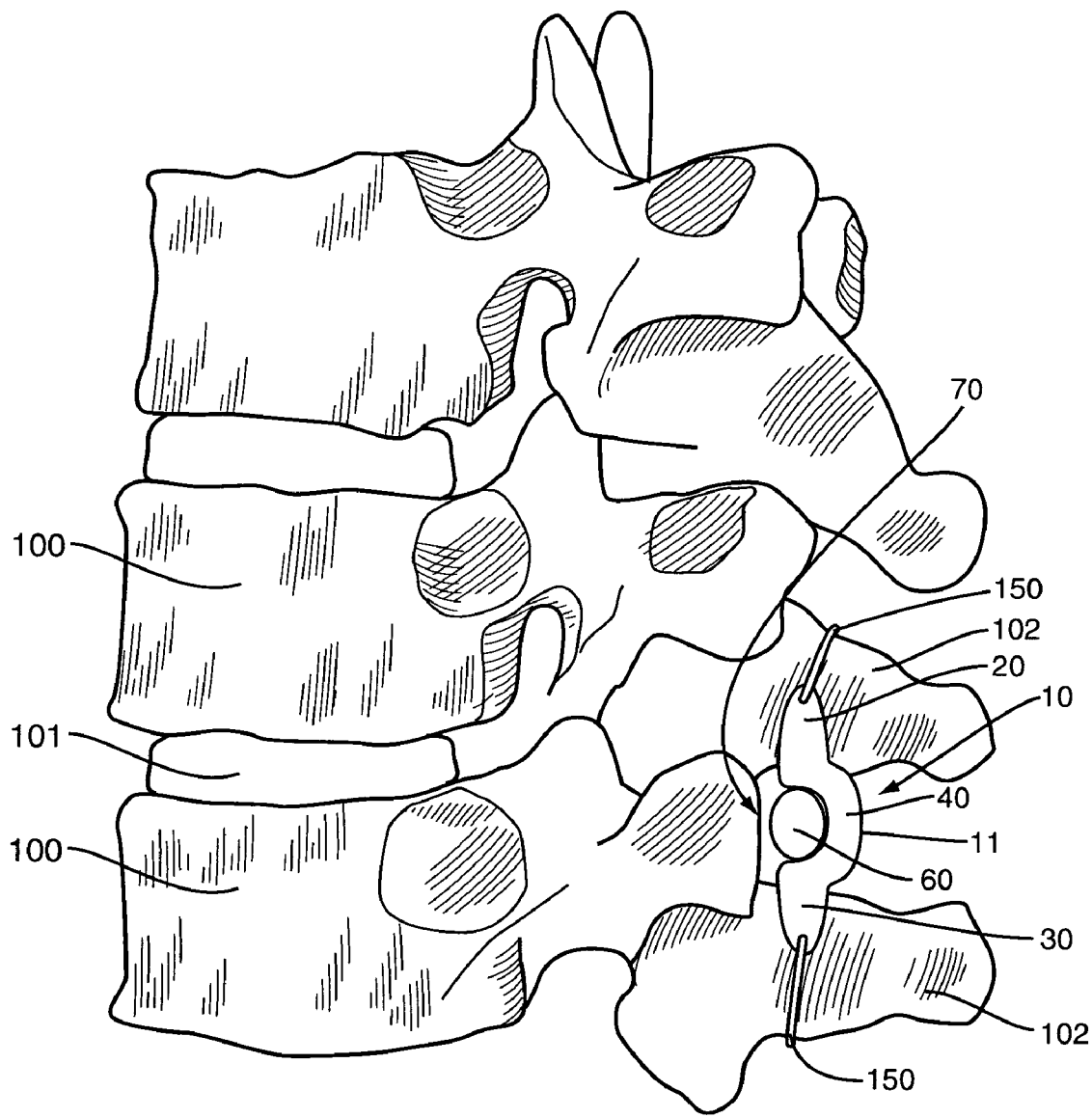
FIG. 1 is a side view of a device positioned between adjacent spinous processes according to one embodiment.

FIG. 1 illustrates one embodiment of a device 10 positioned between the spinous processes 102 of adjacent vertebral members 100. The device 10 in this embodiment includes a body 11 comprising an upper section 20, a lower section 30, and an intermediate section 40. Upper and lower sections 20, 30 are each shaped and sized to contact one of the spinous processes 102. Intermediate section 40 spaces apart the upper and lower sections 20, 30 forming an interior section 70. An elastic member 60 is positioned within the interior section 70. The elastic member 60 and intermediate section 40 are elastically flexible to stabilize the vertebral members 100.

In one embodiment, the intermediate section 40 and elastic member 60 provide variable resistance during movement of the vertebral members 100. The resistance may provide dynamic stabilization during a normal range of motion from the neutral position during flexion, extension, lateral bending, and rotation. The stiffness of the intermediate section 40 and elastic member 60 may further limit the range of motion beyond a predetermined amount.

Body 11 comprises the upper and lower sections 20, 30 and the intermediate section 40. In one embodiment such as illustrated in FIG. 1, the body 11 is constructed of a single member having a folded configuration. In other embodiments, body 11 is constructed of two or more different members. FIG. 2 illustrates one embodiment with the intermediate section 40 constructed of a separate piece that is attached to the sections 20, 30. Upper section 20 is attached to the member 18 with one or more fasteners 90. Embodiments of fasteners 90 may include rivets, pins, screws, etc. Lower section 30 is attached to the member 18 in another manner, such as with adhesives, welding, brazing, etc. FIG. 3 illustrates another embodiment with the intermediate section 40 constructed of two separate members 18a, 18b. In this embodiment, first member 18a is integral with section 20, and second member 18b is integral with section 30. Members 18a, 18b are connected together in a manner as described above. Body 11 may be constructed of a variety of materials including metals, polymers, ceramics, and combinations thereof. Examples of metals include titanium, titanium alloys such as nickel-titanium, stainless steel, and cobalt chromium. Examples of polymers include silicone, silicone-polyurethane copolymer, polyolefin rubber, PEEK, PEEK-carbon composites, polyimide, polyetherimide, polyurethane, and combinations thereof. Examples of polyurethanes include thermoplastic polyurethanes, aliphatic polyurethanes, segmented polyurethanes, hydrophilic polyurethanes, polyether-urethane, polycarbonate-urethane, silicone polyetherurethane, polyvinyl alcohol hydrogel, polyacrylamide hydrogel, and polyacrylic hydrogel. Examples of ceramics include calcium phosphate, hydroxyapatite, HAPCP, alumina, and zirconium. Various shapes, sizes, materials, and constructions for interspinous spacers are disclosed in U.S. patent application Ser. No. 10/851,889 herein incorporated by reference.

Sections 20, 30 are shaped to contact the spinous processes 102 of the vertebral members 100. In one embodiment as illustrated in FIGS. 4 and 5, upper section 20 includes a base 24 and upwardly-extending first and second arms 21, 22. A gap 23 is formed between the arms 21, 22 and the base 24 and is sized to receive the spinous process 102. In this embodiment, the lower section 30 has substantially the same shape and size with a base 34 and upwardly-extending first and second arms 31, 32. A gap 33 is formed between the arms 31, 32 and the base 34 and is sized to receive the spinous process 102.

Figure 6:
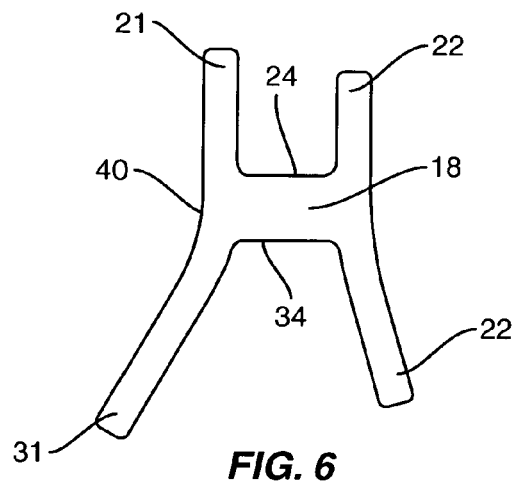
FIG. 6 is a rear view of a device according to one embodiment.

In one embodiment as illustrated in FIG. 5, the arms 21, 22 of the upper section 20 are substantially the same as the arms 31, 32 of the lower section 30. In other embodiments, arms 21, 22 have different heights than arms 31, 32. FIG. 6 illustrates one embodiment with arms 21, 22 have a lesser height than arms 31, 32. Arms may be substantially parallel as illustrated by the arms 21, 22 and 31, 32 of FIG. 5. In another embodiment, arms are non-parallel as illustrated by arms 31, 32 in FIG. 6. Arms may further have the same or different thicknesses.

In one embodiment, upper and lower sections 20, 30 are constructed of flexible materials that allow for the arms 21, 22, 31, 32 to elastically flex to accommodate the spinous processes. When the body 11 is in a neutral configuration with no external forces acting on it, gaps 23, 33 may be the same size, or may have different sizes. Bases 24, 34 may have the same lengths such as the embodiment illustrated in FIGS. 2 and 3. In another embodiment, bases 24, 34 have different lengths as illustrated in FIG. 7.

Figure 7:
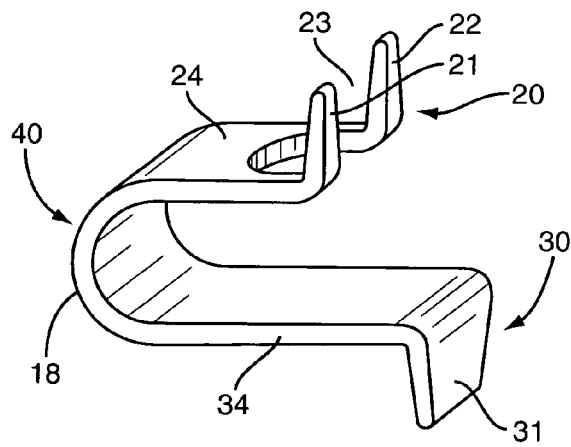
FIG. 7 is a perspective view of a body according to one embodiment.

One embodiment illustrated in FIG. 7 includes the upper section 20 having a split configuration. Gap 23 extends between the arms 21, 22, and a length of the base 24. In one embodiment, the two sections of the base 24 are spaced away a distance for each to contact and support the spinous process 102. In one embodiment, lower section 30 may be formed as a single section (i.e., without a gap 33). In one embodiment, base 34 may have an extended length with the single arm 31 positioned on a posterior edge of the spinous process 102.

Bases 24, 34 may be positioned at a variety of relative angular positions when no external forces are applied to the body 11. In one embodiment, bases 24, 34 are substantially parallel. In another embodiment, the bases 24, 34 angle outward from the intermediate section 40 such that a height of the interior section 70 is less near the intermediate section 40 and increases towards the ends of the bases 24, 34. In another embodiment, bases 24, 34 angle inward as they extend from the intermediate section 40.

Figure 11:
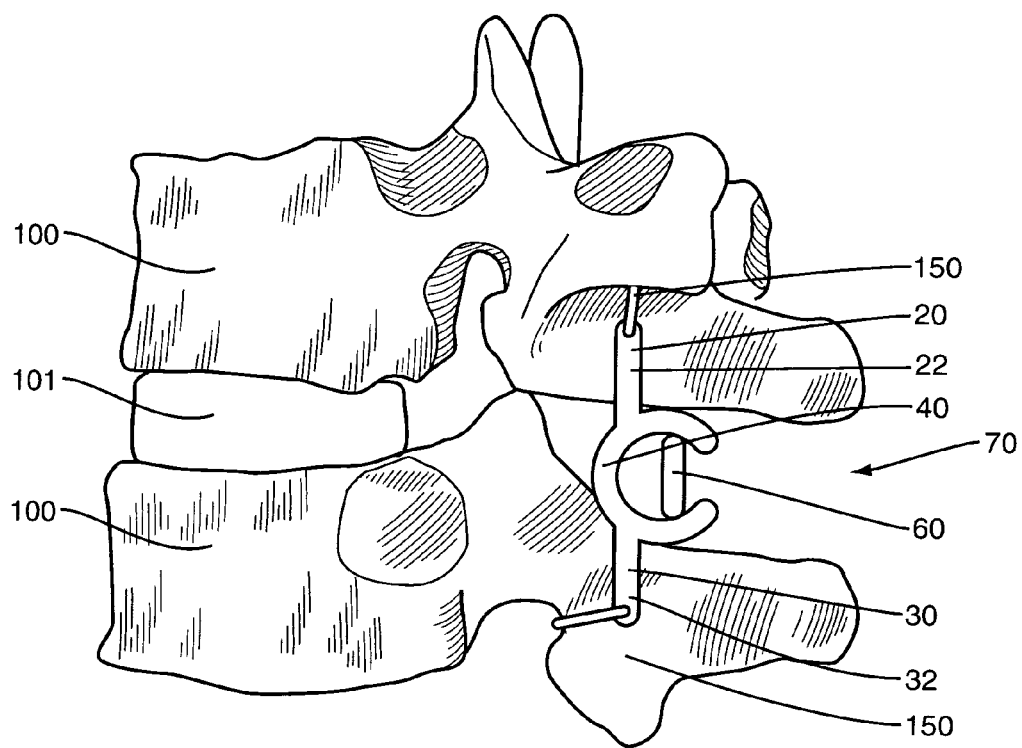
FIG. 11 is a side view of a device positioned between adjacent spinous processes according to one embodiment.

Arms 21, 22, 31, 32 may be positioned at a variety of locations relative to the respective bases 24, 34. In one embodiment as illustrated in FIGS. 2 and 3, arms 21, 31 are positioned at the ends of the bases 24, 34 away from the intermediate section 40. In another embodiment as illustrated in FIG. 11, arms 22, 32 are positioned towards the intermediate section 40 and away from the ends of the bases. In one embodiment, the arms of each base (e.g., arms 21, 22) are positioned at the same location relative to the intermediate section 40. In another embodiment, arms are positioned at different relative locations from the intermediate section 40.

Figure 8:
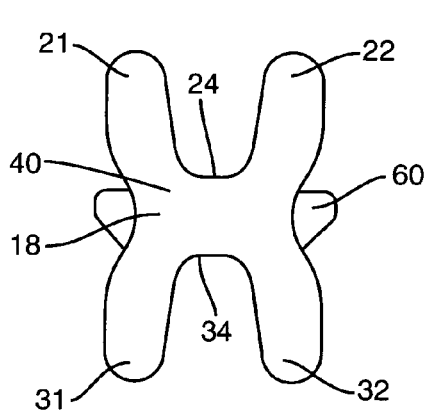
FIG. 8 is a rear view of a device according to one embodiment.
Figure 9:
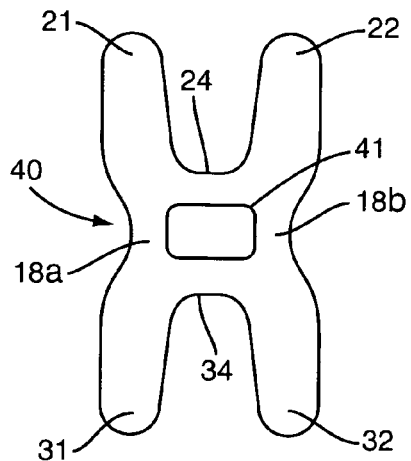
FIG. 9 is a rear view of a device according to one embodiment.
Figure 14:
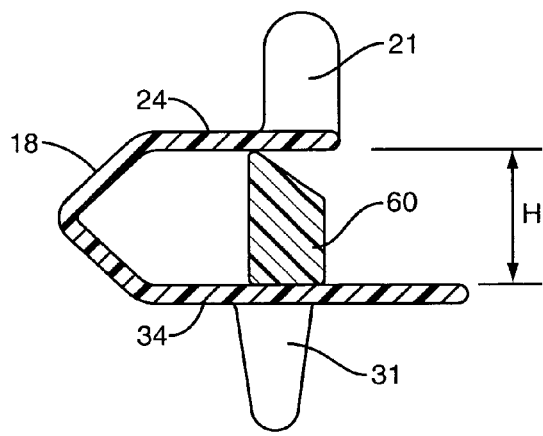
FIG. 14 is a schematic cross section view of a device according to one embodiment.

Intermediate section 40 extends between the sections 20, 30 and provides resistance to movement of the sections 20, 30. Intermediate section 40 may have a variety of shapes. In one embodiment as illustrated in FIG. 14, intermediate section 40 has substantially planar upper and lower sections. In other embodiments, intermediate section 40 has a curved shape as illustrated in FIG. 4. In various other embodiments, intermediate section 40 has a combination of planar and curved shapes. The width of the intermediate section 40 may be substantially the same or different as one or both bases 24, 34. In one embodiment illustrated in FIG. 8, the width of the intermediate section 40 is less than the sections 20, 30. The narrower width may be centered along a centerline of the body 11, or may be off-center. FIG. 5 illustrates an embodiment with the intermediate section 40 having substantially the same width as the sections 20, 30. The thickness of the intermediate section 40 may be the same or different as one or both sections 20, 30. In one embodiment as illustrated in FIG. 9, intermediate section 40 comprises two separate spaced-apart members 18a, 18b. An opening 41 may be formed between the members 18a, 18b.

Figure 10A:
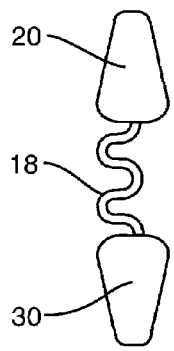
FIGS. 10A-H are side schematic views of bodies according to various embodiments.
Figure 10B:
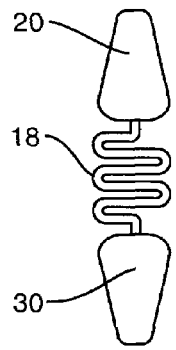
Figure 10C:
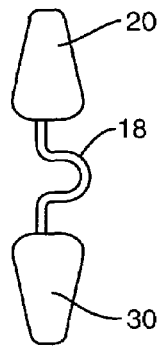
Figure 10D:
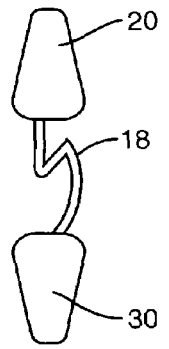
Figure 10E:
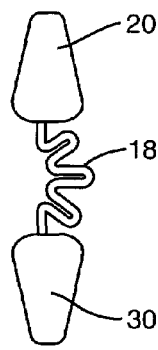

In some embodiments, intermediate section 40 is constructed from a single member 18. FIGS. 10A and 10B illustrate embodiments with the intermediate section 40 having a curved shape. FIGS. 10C, 10D, and 10E illustrate embodiments having an intermediate section 40 comprised of planar and curved sections.

Figure 10F:
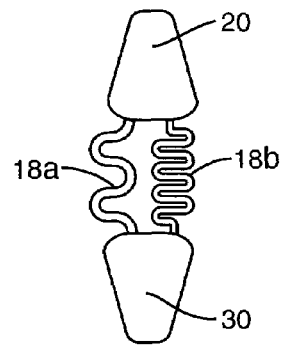
Figure 10G:
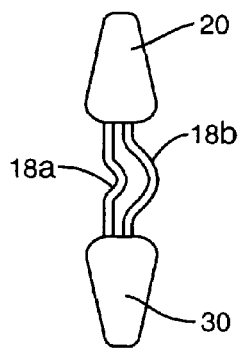
Figure 10H:
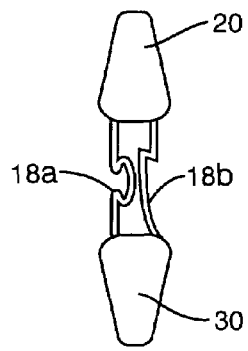

Embodiments of the intermediate section 40 may include multiple members 18. FIG. 10F illustrates an embodiment with a curved first support member 18a and a second support member 18b. FIGS. 10G and 10H illustrate embodiments with first and second members 18a, 18b each including curved and planar sections. In embodiments having multiple members 18, members 18 may be constructed in a unitary fashion, or from multiple different members fastened together.

Support members 18 may also have an overlapping configuration. The overlap may be in a horizontal direction, vertical direction, or both. Member 18 of FIG. 10A and members 18a and 18b of FIG. 10G illustrate embodiments having vertical overlap with multiple sections of the member 18 being in overlap. FIGS. 10B, 10C, 10D, and 10E also include vertical overlap. FIGS. 10D and 10E illustrate embodiments of horizontal overlap with members 18a, 18b being horizontally positioned. Some embodiments feature both horizontal and vertical overlap. Intermediate sections 40 comprising multiple members 18 include horizontal overlap due to the construction. Each of the members 18 may themselves include horizontal and/or vertical overlap.

Figure 12:
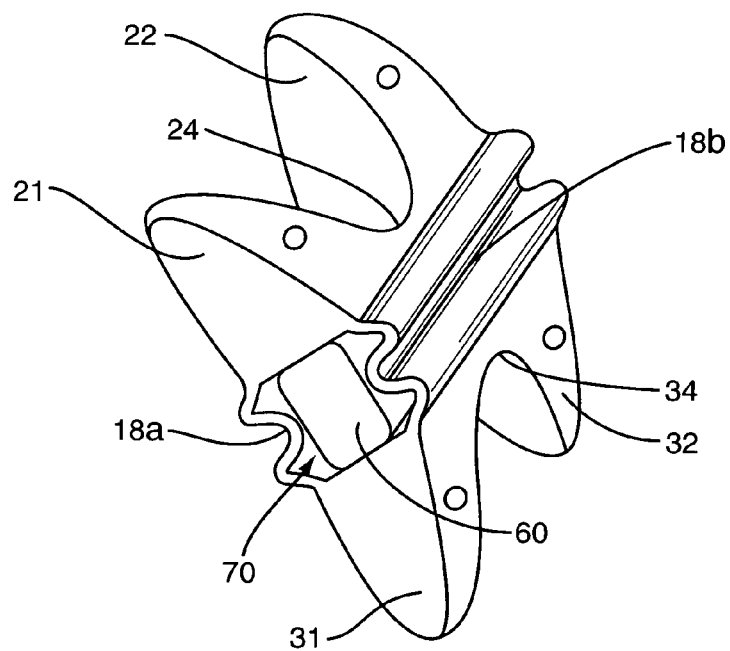
FIG. 12 is a perspective view of a body according to one embodiment.

In one embodiment as illustrated in FIG. 1, intermediate section 40 is positioned on a posterior side of the body 11. An opening into the interior section 70 faces in an anterior direction. In another embodiment as illustrated in FIG. 11, the intermediate section 40 is positioned on an anterior side of the body 11 with the opening into the interior section 70 facing in the posterior direction. FIG. 12 illustrates another embodiment with a more enclosed interior section 70. Intermediate section 40 includes members 18a, 18b that extend from the bases 24, 34 around the posterior and anterior sides of the interior section 70. The members 18a, 18b may have a variety of shapes and constructions as described above. In the embodiments of FIGS. 1, 11, and 12, the lateral sides of the interior section 70 are open. In other embodiments, one or both lateral sides may be closed.

Elastic member 60 is positioned within the interior space 14 and has a stiffness to provide resistance and resist movement of the sections 20, 30. The elastic member 60 shares the load applied to the device and may prevent fatigue failure of the intermediate section 40. The elastic member 60 may impose a substantially linear or non-linear resistance to resist movement of the sections 20, 30.

Elastic member 60 may be constructed of a variety of different materials. Member 60 may be resilient and change shape during movement of the sections 20, 30. Examples of such materials include elastic or rubbery polymers, hydrogels or other hydrophilic polymers, or composites thereof. Particularly suitable elastomers include silicone, polyurethane, copolymers of silicone and polyurethane, polyolefins, such as polyisobutylene and polyisoprene, neoprene, nitrile, vulcanized rubber and combinations thereof. Examples of polyurethanes include thermoplastic polyurethanes, aliphatic polyurethanes, segmented polyurethanes, hydrophilic polyurethanes, polyether-urethane, polycarbonate-urethane and silicone polyetherurethane. Other suitable hydrophilic polymers include polyvinyl alcohol hydrogel, polyacrylamide hydrogel, polyacrylic hydrogel, poly(N-vinyl-2-pyrrolidone hydrogel, polyhydroxyethyl methacrylate hydrogel, and naturally occurring materials such as collagen and polysaccharides, such as hyaluronic acid and cross-linked carboxyl-containing polysaccharides, and combinations thereof.

Elastic member 60 may be connected to the body 11, or may be freely positioned within the interior section 70. In one embodiment, elastic member 60 is connected to one or more of the sections 20, 30 and intermediate section 40. The elastic member 60 may be connected with mechanical fasteners such as screws, pins, rivets, etc. In another embodiment, elastic member 60 is connected to the body 11 with an adhesive. In one embodiment, the inner edges of one or more of the sections 20, 30 and intermediate section 40 include a roughened surface, ridges, teeth, etc. to maintain the position of the elastic member 60. In one embodiment, the elastic member 60 has a shape that attaches to one or both of the sections 20, 30. In a specific embodiment, elastic member 60 includes a dovetail recess that attaches with an extension that extends from the body 11.

When connected to both endplates 11, 12, the elastic member 60 provides resistance to both inward and outward movement. During inward movement of the endplates 11, 12, elastic member 60 is compressed and provides a resistance to the inward movement. During outward movement of the endplates 11, 12, the elastic member 20 is placed in tension to provide resistance. In one embodiment, the elastic member 20 is placed in compression during extension of the vertebral members and placed in tension during flexion.

In one embodiment with the elastic member 60 connected to only one or neither endplate 11 or 12, the elastic member 60 provides resistance to inward movement. The elastic member 60 may not be placed in tension during outward movement and the resistance to this movement is limited to the intermediate section 40.

Figure 13A:
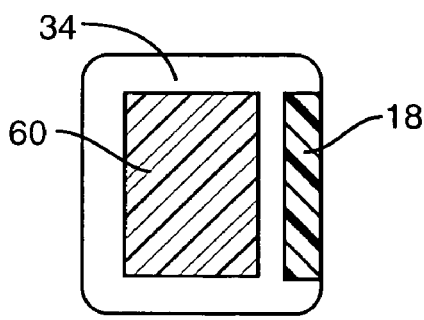
FIGS. 13A-F are schematic cross section views of elastic members according to various embodiments.
Figure 13B:
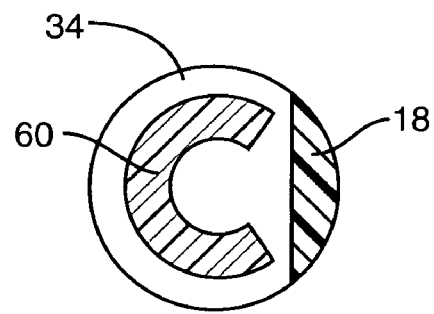
Figure 13C:
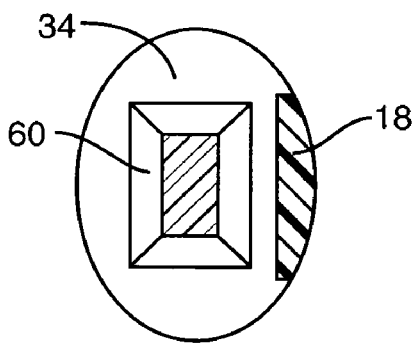
Figure 13D:
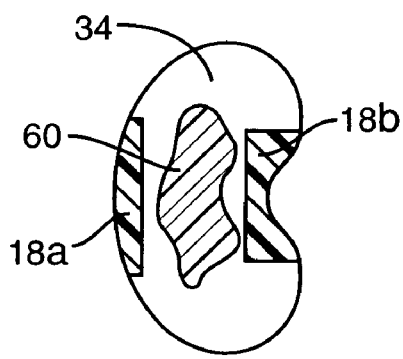

In various embodiments, elastic member 60 is constructed from a single member as illustrated in FIGS. 13A-13D. FIG. 13A illustrates one embodiment having an elastic member 60 with a substantially rectangular shape. FIG. 13B illustrates a substantially C-shaped elastic member 60 with the base facing away from the support member 18. FIG. 13C illustrates an elastic member 60 having a rectangular first surface that contacts the section 30 and four planar sidewalls that taper upwards. FIG. 13D illustrates an embodiment having an irregular, non-symmetrical shape.

Figure 13E:
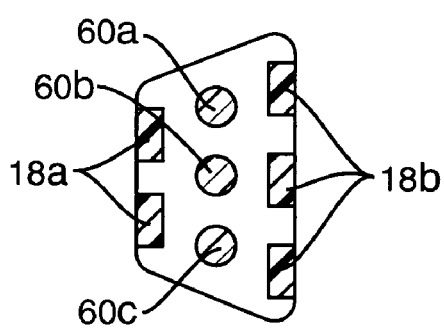
Figure 13F:
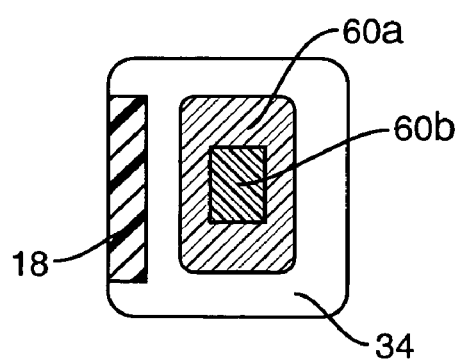

Elastic member 60 may further include two or more separate members. The separate members may have the same construction, or may be constructed of different materials each having a different stiffness. FIG. 13E illustrates an embodiment having three separate elastic members 60a, 60b, 60c. Each elastic member 60a, 60b, 60c is independent and has a substantially circular shape that may be cylindrical, spherical, or conical. FIG. 13F illustrates an embodiment having a first elastic member 60a that extends around a second elastic member 60b. In one embodiment, elastic members 60a, 60b are connected together.

In a neutral condition with no external forces on the body 11, the elastic member 60 may have a variety of heights H. In one embodiment, the height H is sized for the member 20 to extend between and contact both sections 20, 30. In one embodiment, the height H may be substantially the same throughout the elastic member 60. In other embodiments as illustrated in FIGS. 14 and 15, the height H may vary along the elastic member 60.

Figure 15:
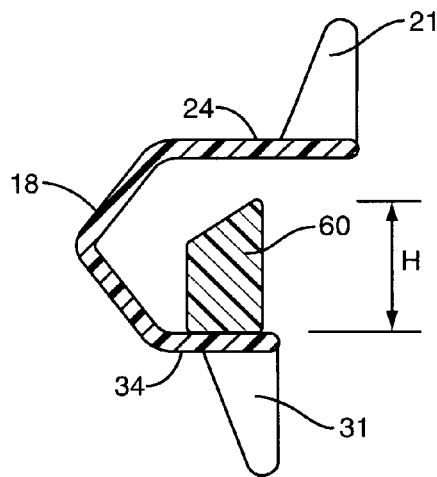
FIG. 15 is a schematic cross section view of a device according to one embodiment.

FIG. 14 includes elastic member 60 having a height that decreases away from the support member 18, and FIG. 15 includes the elastic member 60 having a height the increases away from the support member 18.

The device 10 may provide a variable resistance to deformation. The variable resistance may cause less resistance to initial amounts of vertebral movement, but apply greater forces to reduce larger vertebral movements. By way of example, the device 10 may be designed to provide little resistance during an initial amount of movement of the sections 20, 30. Larger amounts of resistance may be applied to the vertebral members when the sections 20, 30 move beyond the initial amount. In some embodiments, the stiffness of the elastic member 60 and intermediate section 40 increases with additional amounts of movement. The amount of resistance applied by each member increases the further they move away from the original, first position.

Variable resistance to inward movement may also result from the height of the elastic member 60. In one embodiment, the height H is less than the height of the interior section 70 (i.e., the member 60 does not contact both sections 20, 30). The resistance to the initial movement of the sections 20, 30 is isolated to the intermediate section 40. The elastic member 60 does not affect the stiffness until it is contacted by both sections 20, 30 and begins to elastically deform. In one embodiment, deformation is limited to the intermediate section 40 during an amount of initial section movement. Movement beyond this initial amount causes the sections 20, 30 to begin deforming the elastic member 60 in addition to continued deformation of the intermediate section 40 resulting in greater stiffness of the device and more resistance to additional movement.

The shape and size of the elastic member 60 may further cause variable resistance to deformation. Greater amounts of contact between the sections 20, 30 and the elastic member 60 may result in greater amounts of resistance. By way of example using the embodiments of FIGS. 14 and 15, the peaked shapes of the elastic members 20 provides less resistance during initial amounts of inward movement of the sections 20, 30. Additional inward movement of the sections 20, 30 results in deformation of larger amounts of the elastic member 60 resulting in greater resistance.

Figure 16:
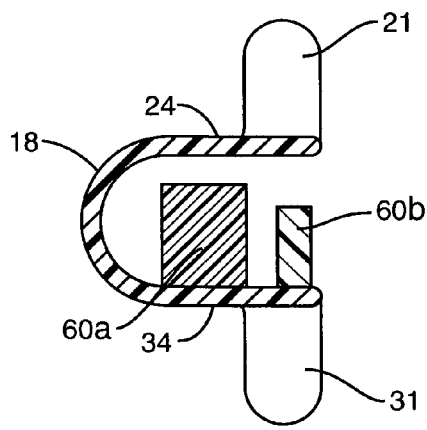
FIG. 16 is a schematic cross section view of a device according to one embodiment.

Variable resistance may also be provided by multiple elastic elements. FIG. 16 illustrates an embodiment having two separate elastic members 60a and 60b. During inward movement of the sections 20, 30, the inner elastic member 60a is initially contacted thus causing a first amount of resistance. The second elastic member 60b is not contacted by the section 20 until the sections 20, 30 are compressed beyond a predetermined amount. This compression then causes the elastic member 60b to deform resulting in additional amounts of resistance. In this embodiment, elastic members 60a, 60b may have the same or different stiffnesses.

Figure 17:
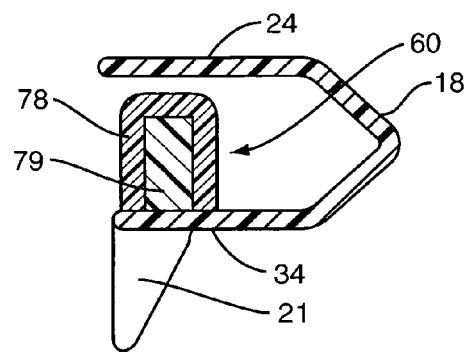
FIG. 17 is a schematic cross section view of a device according to one embodiment.

FIG. 17 illustrates an embodiment having a single elastic member 60 constructed of first and second materials 78, 79 having a different stiffness. Initial compression of the sections 20, 30 causes deformation of the first material 78 resulting in a first resistance. Additional compression causes deformation of the first and second materials 78, 79 which together provide additional resistance.

FIGS. 22A and 22B illustrate another embodiment having first and second members 60a, 60b positioned between the bases 24, 34. As illustrated in FIG. 22A, member 60b has a greater length and is in a slackened configuration when the device is in a neutral orientation with no external forces. An initial outward movement of the bases 24, 34 is resisted initially by the first member 60a and the intermediate section 40. As the bases 24, 34 move outward, member 60b is pulled tight. Movement beyond this amount causes the member 60b to be stretched and resist to further movement is opposed by first and second members 60a, 60b and the intermediate section 40. Members 60a, 60b may be constructed of the same or different materials. In one embodiment, member 60b is constructed of an inelastic material and acts as a limiter to control the extent of outward movement. The bases 24, 34 may be moved apart an amount until the member 60b is pulled tight. The inelastic nature of the member 60b then prevents further outward movement of the bases 24, 34 beyond this amount.

Figure 18:
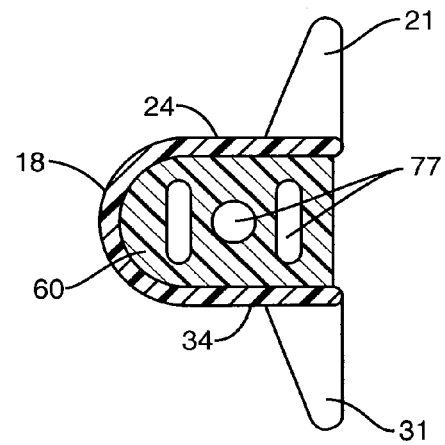
FIG. 18 is a schematic cross section view of a device according to one embodiment.
Figure 19:
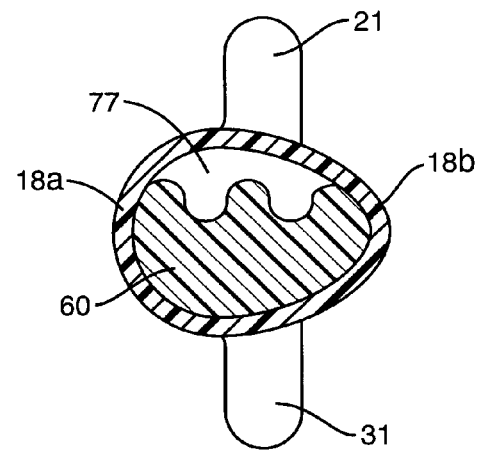
FIG. 19 is a schematic cross section view of a device according to one embodiment.

Elastic member 60 may fill varying amounts of the interior section 70. In one embodiment, member 60 fills a limited amount of the interior section 70. In another embodiment as illustrated in FIGS. 18 and 19, elastic members 60 substantially fill the entirety of the interior section 70. In the embodiments of FIGS. 18 and 19, voids 77 are positioned within the elastic member 60. In one embodiment, voids have a specific shape and size to control the supporting abilities of the elastic member 60. Voids 77 may be substantially free of material, or may be filled with a material that is different than that of the elastic member 60. As illustrated in FIG. 18, voids 77 may be positioned within the interior of the elastic member 60, or may be positioned along one edge as illustrated in FIG. 19.

In one embodiment, elastic member 60 is positioned completely within the interior section 70. In other embodiments, elastic member 60 is positioned within the interior section 70 and extends outward from one or more sides.

A limiter may prevent movement of the sections 20, 30 beyond a predetermined amount. FIG. 20 illustrates one embodiment having a rigid limiting member 90 positioned within the interior section 70. Inward movement of the sections 20, 30 causes deformation of the elastic members 60a, 60b. At a predetermined amount of movement, a top edge of limiting member 90 contacts the section 20 and prevents further inward movement. Limiting member 90 may have a variety of different shapes and orientations.

Another limiting embodiment is illustrated in FIGS. 21A and 21B. Sections 20, 30 are formed with ends 28, 38 positioned along the bases 24, 34 opposite from the intermediate section 40. In a first position as illustrated in FIG. 21A, ends 28, 38 are spaced apart. This allows for inward movement of the sections 20, 30 during vertebral movement. At a predetermined amount of inward movement, ends 28, 38 contact together as illustrated in FIG. 21B and further inward movement is prevented.

In one embodiment, one or both sections 20, 30 are constructed to have increased contact with the vertebral members. In one embodiment, the sections 20, 30 are constructed of a porous material. In another embodiment, sections 20, 30 are textured. In still other embodiments, sections 20, 30 include spikes or serrations. In one embodiment, one or both sections 20, 30 may be coated with osteo-conductive material. Embodiments of the material may include hydroxyapatite and BMP.

In some embodiments as illustrated in FIGS. 1 and 11, one or more tethers 150 may further attach the device 10 to the spinous processes 102. In one embodiment, tethers 150 are attached to the arms 21, 22, 31, 32 and extend around the spinous process 102. Tether 150 may be constructed from materials that are elastic, semi-elastic, or inelastic. Tether 150 may be solid, such as constructed from silicone, may be braided or woven, such as a polyester braid or weave, or may be a combination of different materials and constructions.

Figure 24:
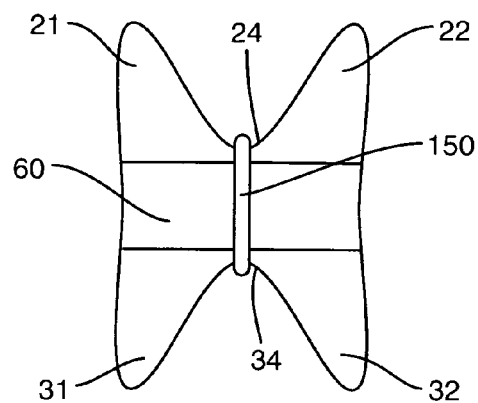
FIG. 24 is a rear or front schematic view of a device with a tether according to one embodiment.
Figure 26:
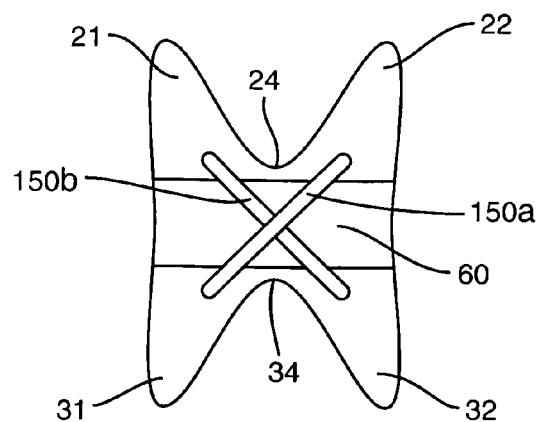
FIG. 26 is a rear or front schematic view of a device with a tether according to one embodiment.

Tethers 150 may also be used to provide additional resistance to device 10. In one embodiment as illustrated in the embodiments of FIGS. 23 and 24, tether 150 extends across the opening into the interior section 70. In one embodiment, tether 150 has a narrow width as illustrated in FIG. 24. In another embodiment, tether 150 is wider, and may even extend across the entire width of the opening into the interior section 70. In one embodiment, a single tether 150 extends across the opening. In other embodiments as illustrated in FIG. 26, multiple tethers 150 may extend across the opening.

Figure 25:
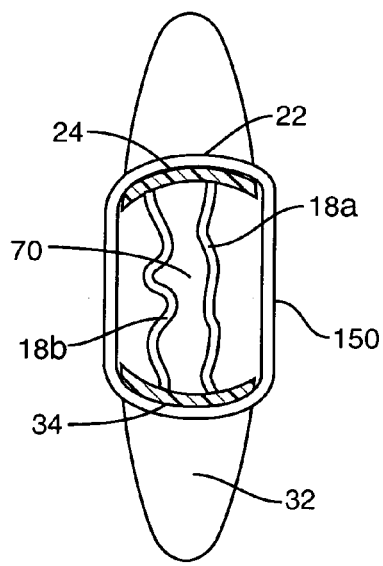
FIG. 25 is a side schematic view of a device with a tether according to one embodiment.

FIG. 25 illustrates an embodiment with the tether 150 extend around the intermediate section 40 and bases 24, 34. This tether 150 may be constructed of a single, continuous band, or multiple members connected together.

Tether 150 may function to contain the elastic member 60, and may also provide resistance during vertebral movement. In one embodiment, tether 150 is constructed of an elastic material that stretches upon movement of the vertebral members 100. In one embodiment, tether 150 is constructed of an inelastic material to prevent movement beyond a predetermined amount. In another embodiment, one or more tethers 150 are connected to the elastic member 60. In one embodiment, the tether 150 is completely contained within the elastic member 60. In one embodiment, tether 150 is positioned completely or in part on the exterior surface of the elastic member 60. In another embodiment, tether 150 extends outward from the elastic member 60. The tether or tethers 150 connected to the elastic member 60 may provide additional resistance during vertebral movement.

Vertebral movement may cause relative movement of the sections 20, 30. The terms "inward movement", "outward movement", and the like are used herein in a general sense to describe the general motion of the sections 20, 30 that reduces and enlarges the distance between the sections 20, 30. The sections 20, 30 may move directly towards one another during this movement, or there may be some lateral component to the movement. Further, the vertebral movement may cause movement of one or both of the sections 20, 30.

Spatially relative terms such as "under", "below", "lower", "over", "upper", "lower", "intermediate", and the like, are used for ease of description to explain the relative positioning of elements. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An interspinous device for positioning between first and second vertebral members, the device comprising:
    an upper section sized to contact the first vertebral member;
    a lower section sized to contact the second vertebral member;
    a first intermediate section extending between anterior sections of the upper and lower sections;
    a second intermediate section extending between posterior sections of the upper and lower sections, the second intermediate section being independent of and spaced away from the first intermediate member;
    an interior section formed between the first and second intermediate sections;
    an elastic member positioned within the interior section;
    the first and second intermediate sections and the elastic member providing resistance to movement of the vertebral members;
    at least one of the first and second intermediate sections includes multiple turns with at least three of the turns being vertically overlapping;
    at least one of the first and second intermediate sections includes a different shape than the elastic member.

2. The device of claim 1, wherein the interior section has open lateral sides.

* * * * *